(12) United States Patent
Cheung et al.

(10) Patent No.: US 8,161,596 B2
(45) Date of Patent: Apr. 24, 2012

(54) TILT SENSOR FOR CLEANING DEVICE

(75) Inventors: William K. Y. Cheung, Yuen Long (HK); Ernest Matthew Chavana, Jr., Cookesville, TN (US)

(73) Assignee: Oreck Holdings LLC, Nashville, TN (US)

( * ) Notice: Subject to any disclaimer, the term of this patent is extended or adjusted under 35 U.S.C. 154(b) by 505 days.

(21) Appl. No.: 12/359,097

(22) Filed: Jan. 23, 2009

(65) Prior Publication Data

US 2010/0186187 A1    Jul. 29, 2010

(51) Int. Cl.
*A47L 7/00* (2006.01)
*G01J 1/44* (2006.01)

(52) U.S. Cl. ........................................ 15/339; 356/139.1

(58) Field of Classification Search .................... 15/319, 15/339; 356/139.1; 250/206, 214 R, 231.1, 250/222.1; 422/24; *A47L 7/00; G01J 2/00; A61L 2/00; H01J 40/14*
See application file for complete search history.

(56) References Cited

U.S. PATENT DOCUMENTS

| | | | | |
|---|---|---|---|---|
| 4,450,353 A | * | 5/1984 | Sjolund | 250/231.1 |
| 5,202,559 A | * | 4/1993 | Durst | 250/231.1 |
| 5,373,153 A | * | 12/1994 | Cumberledge et al. | 250/231.1 |
| 5,902,999 A | * | 5/1999 | Yanagi et al. | 250/231.1 |
| 6,011,254 A | * | 1/2000 | Sano et al. | 250/231.1 |
| 6,140,635 A | * | 10/2000 | Kazumi et al. | 250/231.1 |
| 6,184,521 B1 | * | 2/2001 | Coffin et al. | 250/237 R |
| 6,392,223 B1 | * | 5/2002 | Hjertman et al. | 250/231.1 |
| 444,711 A1 | | 11/2008 | Garcia et al. | |
| 7,476,885 B2 | | 1/2009 | Garcia et al. | |
| 7,612,877 B2 | * | 11/2009 | Lin | 356/139.1 |
| 2007/0192987 A1 | * | 8/2007 | Garcia et al. | 15/339 |
| 2008/0061252 A1 | | 3/2008 | Garcia et al. | |
| 2008/0256741 A1 | * | 10/2008 | Garcia et al. | 15/319 |

FOREIGN PATENT DOCUMENTS

JP    8-298054    11/1996

* cited by examiner

*Primary Examiner* — David Redding
(74) *Attorney, Agent, or Firm* — Winston & Strawn LLP

(57) ABSTRACT

A tilt sensor for a cleaning device makes use of an optical sensor to interrupt operation of the device. In one implementation, the tilt sensor shuts off a UV light included in the cleaning device's operations. The tilt sensor includes a housing with at least one chamber defined therein. A sliding or moving element is located in the chamber. The optical sensor is operatively associated with the chamber so that, in response to certain movement of the element within the chamber, the optical sensor signals the tilt sensor to turn off the UV light.

17 Claims, 3 Drawing Sheets

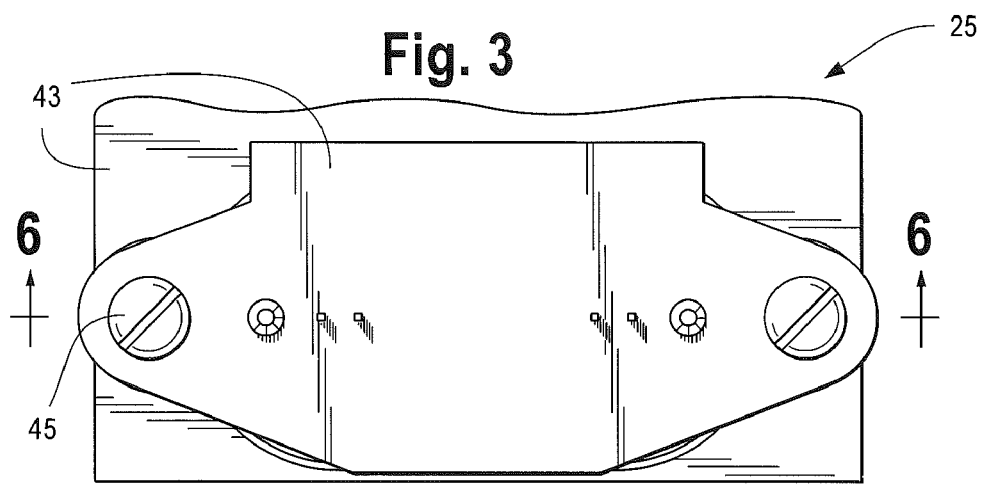
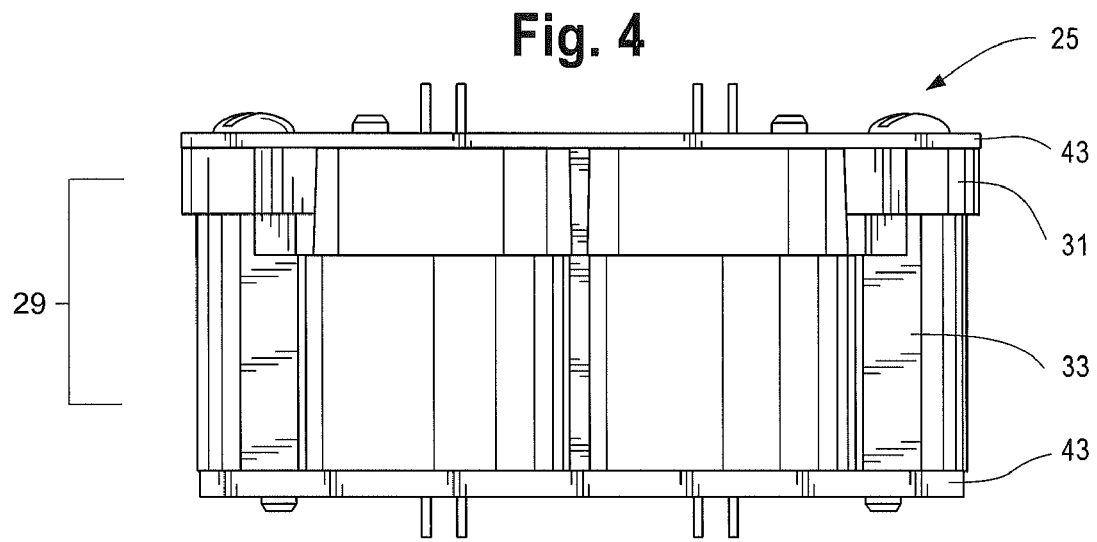
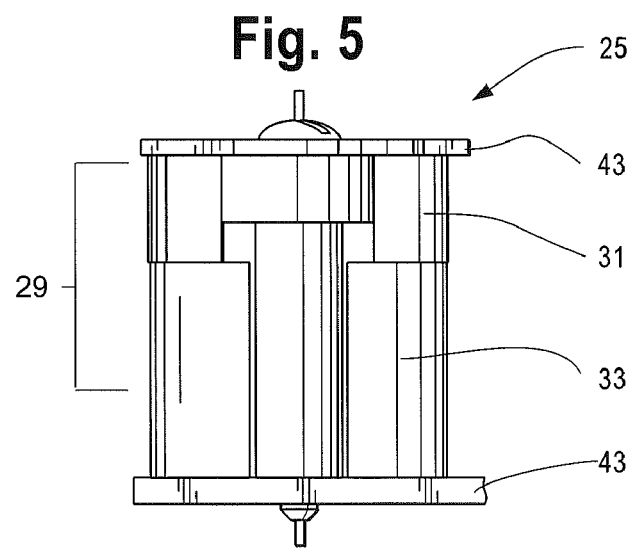

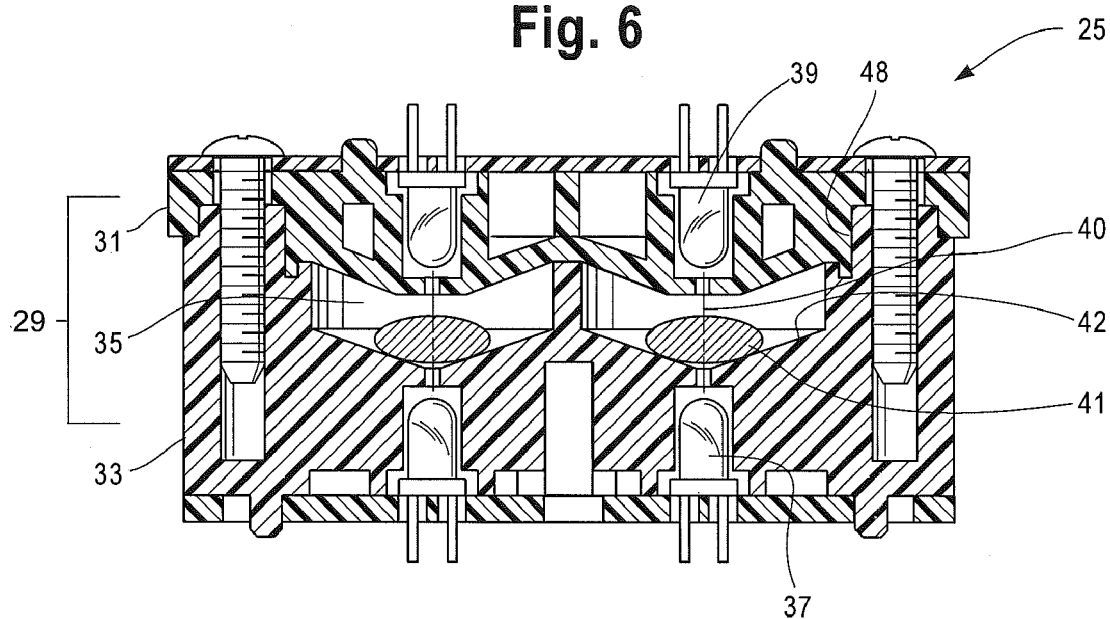
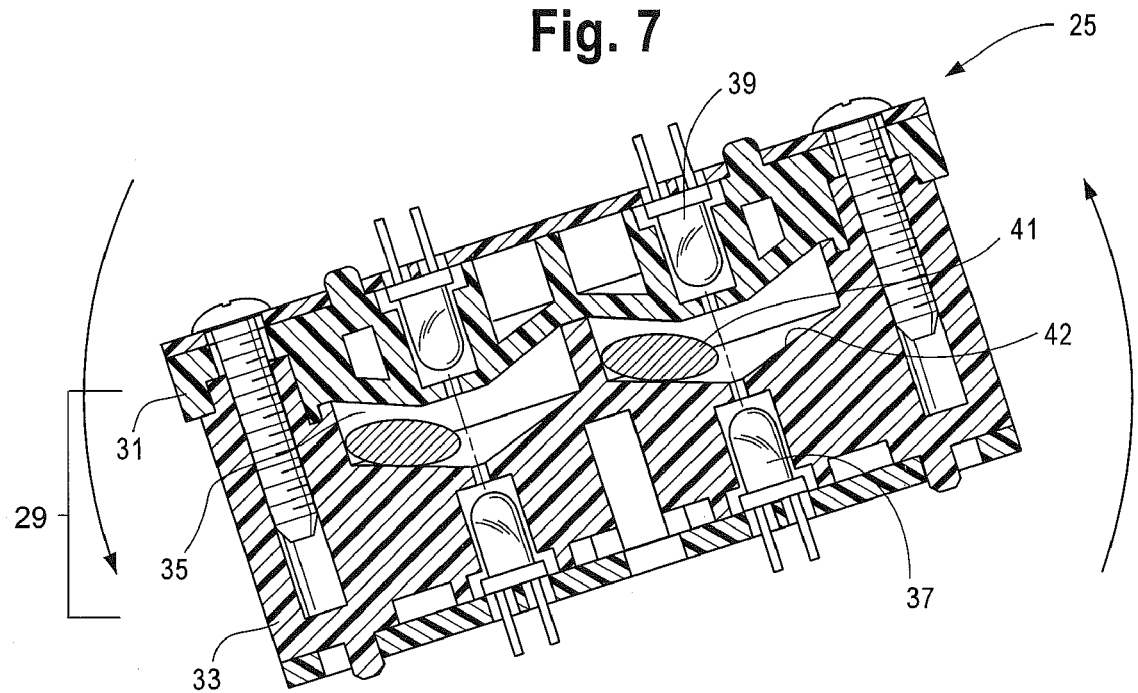

TILT SENSOR FOR CLEANING DEVICE

FIELD

The invention relates to a tilt sensor for a cleaning device.

BACKGROUND

Cleaning devices, such as vacuums, are sometimes equipped with additional operative features associated with their cleaning operations. One such additional feature is the ability to disinfect surface, drapes, or other media while otherwise cleaning, such disinfecting often being accomplished by means of UV radiation from a UV light source. One suitable disinfecting vacuum device is disclosed U.S. Patent Application Publication Nos. US-2007/0192987-A1, US-2008/0061252-A1, and U.S. Pat. Nos. 7,444,711, and 7,476,885.

The cleaning device in such disclosures is described as being equipped with switches that turn off the UV light source in response to certain conditions, including tilting of the surface associated with the UV light source. However, such switches often suffer from various drawbacks and disadvantages.

SUMMARY

In one implementation, a cleaning device utilizing a UV light source is equipped with a tilt sensor. When the tilt sensor is horizontal, a sliding element within the tilt sensor blocks light emitted from a photo-emitter. When the angle of the tilt sensor exceeds a predetermined angle relative to horizontal, the sliding element no longer blocks the light emitted from the photo-emitter, and the light reaches a photo-collector, thereby completing a circuit, which shuts off energy to the UV light source. The sensor is thus designed to shut off or deactivate the UV light source in response to a change in inclination of the cleaning device.

According to another implementation, the cleaning device comprises a vacuum, and the tilt sensor comprises a housing securable relative to the vacuum. The housing has a pair of chambers defined therein, an optical sensor located to define a detection zone within each of the chambers to detect variations in light, and an element located in the detection zone of each of the chambers and moveable in response to tilting of the vacuum. The tilt sensor is adapted to interrupt operation of the vacuum in response to the movement of the element. The detection zone may comprise a path between a photo-emitter and a photo-collector of the optical sensor.

The element of the tilt sensor may be configured to move relative to the chamber between a first position fully or partially obstructing the path and a second position less obstructing or not obstructing of the path. The chamber of the tilt sensor includes lower and upper walls, and the path extends between the walls. The lower wall of the tilt sensor slopes downwardly toward the path, the element adapted to be slidable toward the path in the absence of tilting and along the lower wall away from the path in response to sufficient tilting. The housing of the tilt sensor includes two opposing portions secured to each other to define the chamber, the opposing portions having at least two pairs of opposing surfaces defining an angle relative to each other, the angle located between the exterior of the housing and the chamber to inhibit entry of dust from the exterior of the housing into the chambers.

Additional features and advantages of the invention will be made apparent from the following detailed description of illustrative embodiments that proceeds with reference to the accompanying drawings.

BRIEF DESCRIPTION OF THE DRAWINGS

The foregoing summary, as well as the following detailed description of the preferred embodiments, is better understood when read in conjunction with the appended drawings. For the purpose of illustrating the invention, there are shown in the drawings embodiments that are presently preferred, it being understood, however, that the invention is not limited to the specific methods and instrumentalities disclosed. In the drawings:

FIGS. 3-5 are top, side, and end views, respectively, of the tilt sensor of the preceding FIGS;

FIG. 6 is a cross-sectional view taken along line 6-6 of the tilt sensor of FIG. 5;

FIG. 7 is a cross-sectional view similar to FIG. 6, but showing the tilt sensor at an angle relative to horizontal;

DESCRIPTION

Figure 1:
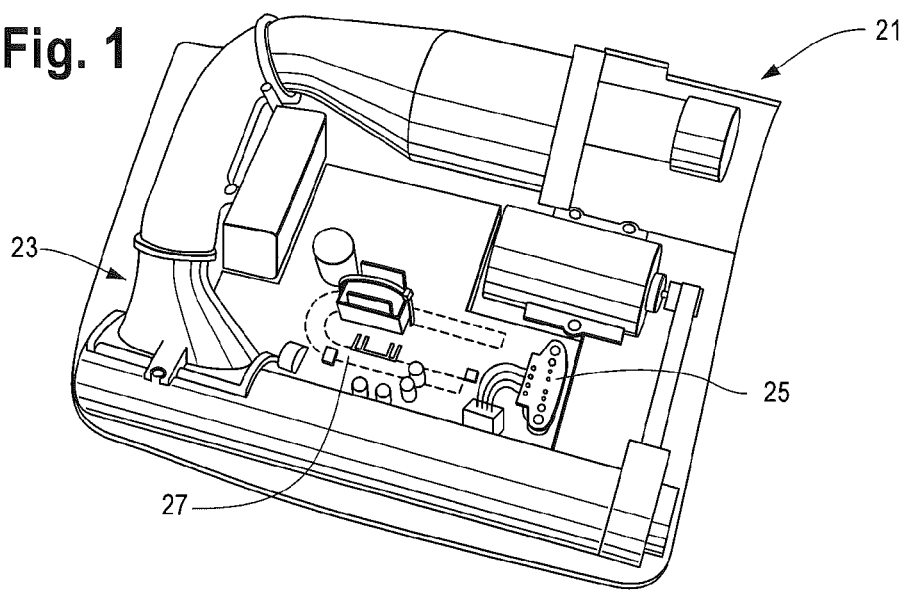
FIG. 1 is a perspective view of one possible implementation of the tilt sensor located in a vacuum cleaner housing assembly.
Figure 2:
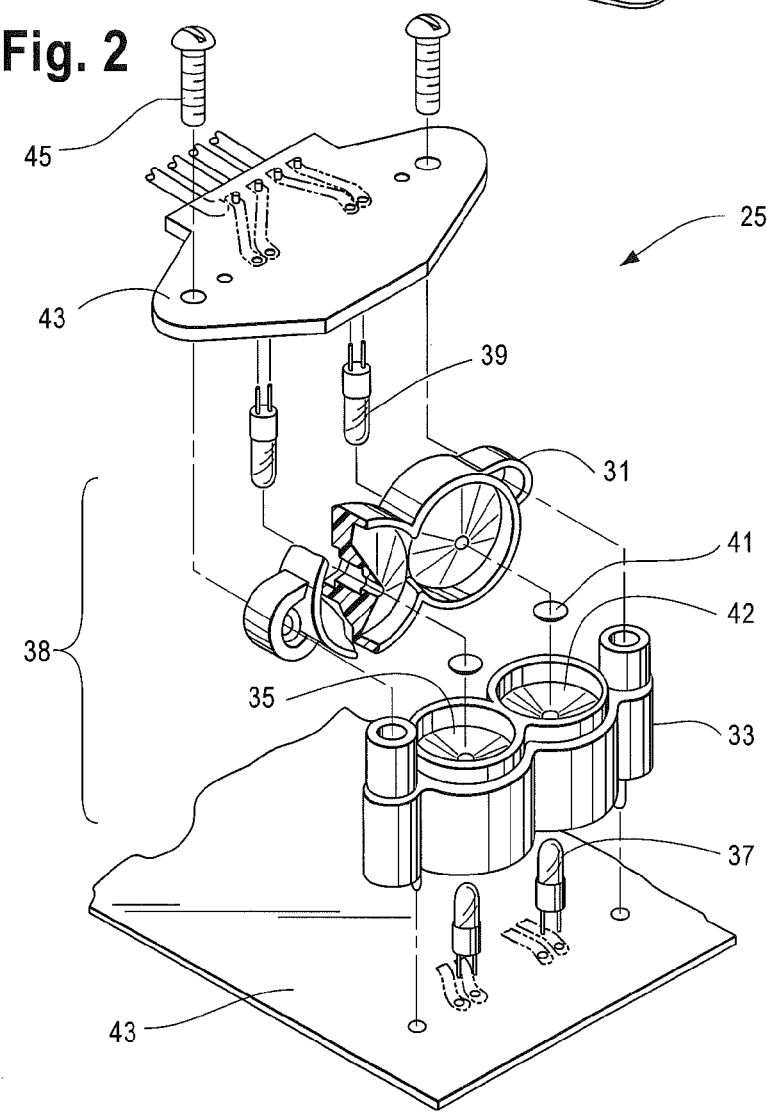
FIG. 2 is an exploded 3 dimensional view of the tilt sensor of FIG. 1.

Referring now to the drawings, and to FIG. 1 in particular, in one possible implementation, cleaning device 21 comprises an upright vacuum equipped with a UV light source 27 mounted to vacuum cleaning base 23, as shown and described in U.S. Patent Publication Nos. 2007/0192987-A1, US-2008/0061252-A1, and U.S. Pat. Nos. 7,444,711, and 7,476,885, the disclosures of which are incorporated by reference herein. Tilt sensor 25 is mounted to base 23 and suitably enclosed by vacuum covers or housing (not shown for purposes of clarify). In this implementation, tilt sensor 25 is horizontal, but it should be appreciated that the location, orientation or angle of tilt sensor 25 can be varied to suit the application or cleaning device parameters. It will be appreciated that cleaning device 21 may assume any number of alternate forms, depending on the characteristics of the media to be cleaned, which media may include any number of floors, rugs, carpets, other surfaces, fabric, materials, furniture, and the like, in the broadest senses of such terms and with limitation thereto.

In the implementation illustrated in FIG. 1, when base 23 is tilted from horizontal by a sufficient amount, such as if the device 21 is raised at an angle off a floor, tilt sensor 25 interrupts operation of device 21, in particular causing UV light 27 to be turned off.

Referring now to FIGS. 2-6, tilt sensor 25 comprises housing 29 with a pair of chambers 35 defined therein. Housing is formed of a top portion 31 and a bottom portion 33. Housing 29 is suitably secured, such as by fasteners 45, to circuit board 43 on top of housing 29, and circuit board 44 on the bottom of housing 29.

Disposed within interior chamber 35 of housing 29 is a sliding element 41. When tilt sensor 25 is horizontal, sliding element 41 is located against bottom surface 42 of chamber 35. Photo-emitters 37 are mounted to direct light from lower portion 33 generally upwardly, to be detected by corresponding photo-collectors 39, which are mounted to receive light directed toward the upper portion 31 of chambers 35. In this way, a light path 40 extends generally vertically across chambers 35. Thus, when sliding element 41 is in the bottom of interior chamber 35 as shown, sliding elements 41 obstruct corresponding light paths 40.

FIG. 7 shows a cross-sectional view of the tilt sensor 25 of FIG. 6, in which tilt sensor 25 is angled relative to horizontal. When the angle with horizontal is sufficient, sliding element 41 moves from its position obstructing light path 40 shown in FIG. 6 to a non-obstructing position in a more radially distant portion of chamber 35. When sliding element 41 is no longer sufficiently obstructing the light emitted from photo-emitter 37, the light is received by photo-collector 39, thereby completing an electronic circuit associated with optical sensor 38 of tilt sensor 25. In response to the electronic circuit being completed, suitable means, such as by an electronic circuit or controller, are provided so that the power to the UV light source 27 (FIG. 1) is shut off.

It should be readily understood that, although, in the illustrated example, the sliding element obstructs the light emitted from the photo-emitter when horizontal, other non-horizontal variations are possible. For example, the placement of the tilt sensor 25 can be altered from the front left side of the vacuum housing 23 as disclosed in FIG. 1, to another non-horizontal location on device 21, which location may require that tilt sensor 25 itself be angled in order to ensure that sliding element 41 moves between first and second positions corresponding to allowing UV light operation and interrupting such operation, respectively. Furthermore, the "angle relative to horizontal" is sufficient to allow sliding element 41 to shift between the two states of operation. Tilt sensor 25 may also be tuned by varying the slope of surface 42 of chambers 35 by adjusting the sensitivities of photo-collectors 39 to respond to total or partial light obstruction, or by adjusting light characteristics of photo-emitters 37.

The photo-emitter/photo-collector pairs comprising a corresponding optical sensor 38 preferably are matched to emit and receive the same light frequency. Suitable optical sensors 38 for this implementation can make use of any frequency of light from within the light spectrum, including gamma, x-ray, UV, visible, infrared, and radio waves. In one possible embodiment, optical sensor 38 uses light waves from the visible light spectrum, and more particularly from about 380 to about 750 nanometer wavelengths. In a preferred embodiment, optical sensor 38 emits light from the infrared spectrum, or more preferably from about 1 millimeter to about 750 nanometer wavelengths.

Housing 29 can be made from any suitable material, so long as there are suitable means for keeping chambers 35 from exposure to stray or ambient light in the operative range of optical sensors 38. For this reason, in one preferred implementation, the material of housing 29 is selected so as not to allow for light transmittance or reflection. Non-limiting suitable materials include steel, aluminum, copper, plastics, resins and polymers. Polymeric materials are available with suitable non-transmittance/non-reflection characteristics. Housing 29 can also be manufactured by a variety of methods, including, but not limited to, being cast, machined, injection molded, and the like. The interior of housing 29, which defines interior chamber 35, is preferably a relatively smooth surface, with a low coefficient of static friction. The outer surface of element 41 is likewise preferably smooth. In this way, friction is reduced between sliding element 41 and interior surfaces of chamber 35. This allows sliding element 41 within interior chamber 35 to respond more consistently to variations in tilt or changes in angle relative to horizontal, and interrupt operation of UV light source 27 when predetermined tilt conditions are met.

Housing 29 comprises upper portion 31 and lower portion 33 that when assembled, define the substantially cylindrical chamber 35. Chamber 35 includes lower and upper walls, and is designed to receive sliding element 41 within a substantially conical portion. The mating surfaces of upper and lower portions 31, 33 define one or more angles to form a tortuous path 48 which inhibits light from outside housing 29 from entering chamber 35. The design of interior chamber 35 prevents sliding element 41 from becoming lodged within chamber 35. Furthermore, housing 29 may comprise two or more interior chambers 35. Multiple chambers allow for redundancy and enhanced safety features of the present disclosure.

The two portions 31 and 33 are secured to each other in order to prevent outside light from entering the interior of tilt sensor 25, and further to prevent exterior dust from entering interior chamber 35. The introduction of exterior light or foreign particles such as duct interferes with the sensitive responsiveness of tilt sensor 25 and optical sensor disclosed herein. Optionally, housing 29 comprises one or more O-rings or washers between the two portions, 31, 33, or is vacuum sealed. Housing 29 may be secured to cleaning device 21, either directly or indirectly, in either a permanent or modular fashion.

Photo-emitter 37 and photo-collector 39 are electrically connected to suitable control or operational circuits so that tilt sensor 25 responds to tilting by a predetermined amount to interrupt operation of cleaning device 21, in this case turning off UV light source 27. Photo-collector 39 may be suitably shielded from exterior light, such as by opaque tape or other opaque covering.

The configurations and dimensions of chamber 35 and sliding elements 41 therein may be varied according to the particular applications intended. In the implementation shown in FIGS. 2-7, sliding element 41 is substantially pill shaped and has a circular horizontal cross-section and has an ellipsoidal vertical cross-section, and chambers 35 have opposing, conical surfaces extended toward respective light paths 40. Element 41 may have an axial height between about 2 and 3 mm, including 2.5 mm, and have a circular cross-section with a diameter of about 7 mm. Elements 41 may likewise be disc-shaped or in the form of spheres in which latter case elements 41 are adapted to roll rather than slide within chambers 35 in response to tilting. The diameter of each of the chambers 35 may be between 14 and 15 mm. For the illustrated implementation, the angle of the conical surfaces of chambers 35 is selected to be about 70 degrees with respect to the vertical axis of the cones defined in the chambers 35. Other angles are possible and suitable, depending on the configuration of the tilt sensor and its intended application.

The distance between the upper and lower surfaces of chambers 35 is selected to allow elements 41 to slide therein, but not so great as to cause element 41 to become jammed or lodged away of its seated position over light path 40 when sensor 21 is tilted. In the illustrated implementation, the height of chambers 35 at the location of light path 40 is about 4.5 mm. Again, any of these dimensions may be "tuned" to change the responsiveness of the tilt sensor to different orientations of cleaning device 21, or to suit different locations or applications of sensor 21.

Sliding element 41 can be made of any suitable material, including by way of non-limiting example, steel, aluminum, copper, plastics, and polymers. Sliding element 41 may be made of the same material as housing 29, or may be made of different material than housing 29.

As described above, various components of tilt sensor 25 containing an optical sensor may be modified and still maintain the spirit of the disclosed preferred embodiments. For example, the different optical sensors may be used, different light frequencies may be utilized, the placement of the tilt sensor may be altered, and three or more chambers may be included in the tilt sensor, etc. Furthermore, tilt sensor 25 containing an optical sensor may also be configured for alternate applications on cleaning device 21, such as for controlling power to a beater bar, rolling brush, or vacuum motor, etc.

It will thus be apparent that there has been provided in accordance with the present invention a disinfecting device comprising a tilt sensor which achieves the aims and advantages specified herein. It will of course be understood that the foregoing description is of preferred exemplary embodiments of the invention and that the invention is not limited to the specific embodiments shown. Various changes and modifications will become apparent to those skilled in the art and all such variations and modifications are intended to come within the spirit and scope of the appended claims.

What is claimed is:

1. A tilt sensor for interrupting operation of a vacuum, the sensor comprising:
    a housing securable relative to the vacuum, the housing having a pair of chambers defined therein;
    an optical sensor located to define a detection zone within each of the chambers in which variations in light are detected;
    an element located in the detection zone of each of the chambers and moveable in response to tilting of the vacuum;
    whereby the tilt sensor is adapted to interrupt operation of the vacuum in response to the movement-of the element, the element is substantially pill-shaped, and the housing comprises non-light transmitting material.

2. The tilt sensor of claim 1, wherein the optical sensor includes a photo-emitter and a photo-collector, and the detection zone comprises a path between the photo-emitter and the photo-collector.

3. The tilt sensor of claim 2, wherein the element is configured to move relative to the chamber between a first position obstructing the path and a second position less or not obstructing of the path.

4. The tilt sensor of claim 3, wherein the chamber includes lower and upper walls, and wherein the path extends between the walls.

5. The tilt sensor of claim 4, wherein the lower wall slopes downwardly toward the path, the element is adapted to be slidable toward the path in the absence of tilting and along the lower wall away from the path in response to sufficient tilting.

6. The tilt sensor of claim 1, wherein the housing includes two opposing portions secured to each other to define the chamber, the opposing portions having at least two pairs of opposing surfaces defining an angle relative to each other, the angle located between the exterior of the housing and the chamber to inhibit entry of dust from the exterior of the housing into the chambers.

7. A tilt sensor for disrupting an electric circuit of a cleaning device, the tilt sensor comprising:
    at least one wall defining at least one chamber therein;
    a photo-emitter and a photo-collector operatively associated with the chamber and the electric circuit;
    an element disposed in the chamber, the element configured to move relative to the photo-emitter in response to predetermined changes in angle relative to horizontal;
    wherein predetermined movement of the element relative to light from said photo-emitter causes said tilt sensor to disrupt the electric circuit, the element is substantially pill-shaped, and the housing comprises non-light transmitting material.

8. The tilt sensor of claim 7, wherein said element is adapted to obstruct light emitted from said photo-emitter when said tilt sensor is horizontal.

9. The tilt sensor of claim 7, wherein said element has a circular horizontal cross-section and has an ellipsoidal vertical cross-section.

10. The tilt sensor of claim 7, wherein the photo-collector is appropriately shielded.

11. The tilt sensor of claim 7, wherein the chamber is adapted to prevent said element from becoming lodged within said chamber.

12. The tilt sensor of claim 7, wherein the photo-collector is further shielded to prevent external sources of light from entering said chamber.

13. The tilt sensor of claim 7, further comprising two chambers.

14. A cleaning device comprising:
    a UV light source for disinfecting a cleaning medium;
    a housing operatively associated with at least one photo-emitter opposite at least one light receiver;
    at least one sliding element adapted to obstruct light emitted from said photo-emitter;
    at least one chamber adapted to prevent said sliding element from obstructing light emitted from said photo-emitter in response to changes in angle relative to horizontal of said housing;
    wherein light received by said photo-collector controls said UV light source, the element is substantially pill-shaped, and the housing comprises non-light transmitting material.

15. The cleaning device of claim 14 wherein light received by said photo-collector shuts off said UV light source.

16. The cleaning device of claim 14 further comprising a vacuum motor.

17. The cleaning device of claim 14 wherein said UV light source is a UV light bulb or plurality of UV light bulbs, and is positioned to emit light onto the cleaning medium.

* * * * *